United States Patent [19]
Scott et al.

[11] Patent Number: 5,629,163
[45] Date of Patent: May 13, 1997

[54] CALCINEURIN INHIBITORY COMPOUNDS AND ANCHORING PROTEIN

[75] Inventors: John D. Scott; Vincent M. Coghlan, both of Portland, Oreg.; Monique L. Howard, Seattle; William M. Gallatin, Mercer Island, both of Wash.

[73] Assignees: ICOS Corporation, Bothell, Wash.; The State of Oregon acting by and through the Oregon State Board of Higher Education and on behalf of Oregon Health Sciences University, Portland, Oreg.

[21] Appl. No.: 452,722

[22] Filed: May 30, 1995

Related U.S. Application Data

[62] Division of Ser. No. 344,227, Nov. 23, 1994.

[51] Int. Cl.$^6$ .................. G01N 33/53; G01N 33/567; C12Q 1/02; C12Q 1/04
[52] U.S. Cl. .................. 435/7.2; 435/29; 435/34; 435/35; 435/7.4; 436/518
[58] Field of Search .................. 514/12–14; 435/29, 435/34–35, 7.4, 7.92, 7.2; 436/518

[56] References Cited

U.S. PATENT DOCUMENTS

| | | | |
|---|---|---|---|
| 4,766,046 | 8/1988 | Abra et al. | 424/450 |
| 5,169,637 | 12/1992 | Lenk et al. | 424/450 |
| 5,180,713 | 1/1993 | Abra | 514/31 |
| 5,185,154 | 2/1993 | Lasic et al. | 424/450 |
| 5,204,112 | 4/1993 | Hope et al. | |
| 5,252,263 | 10/1993 | Hope et al. | 264/4.3 |

FOREIGN PATENT DOCUMENTS

| | | |
|---|---|---|
| 92/02244 | 2/1992 | WIPO. |

OTHER PUBLICATIONS

Aldape, et al., *J.Biol.Chem.* 267:16029–16032 (1992), "Charged Surface Residues of FKBP12 Participate in Formation of the FKBP12–FK506–Calcineurin Complex*".
Bougneres, et al., *N.Eng.J.Med.* 318:663–670 (1988), "Factors Associated With Early Remission Of Type I Diabetes In Children Treated With Cyclosporine".
Canadian Multicenter, *N.Eng.J.Med.* 314:1219–1225 (1986), "A Randomized Clinical Trial Of Cyclosporine In Cadaveric Renal Transplantation".
Carr, et al., *J.Biol. Chem.* 267:16816–16823 (1992), "Localization of the cAMP–dependent Protein Kinase to the Postsynaptic Densities by A–Kinase Anchoring Proteins".
Carr, et al., *J.Biol.Chem.* 267:13376–13382 (1992), "Association of the type II cAMP–dependent Protein Kinase with a Human Thyroid RII–anchoring Protein".
Carr, et al., *J.Biol. Chem;.* 268:20729–20732 (1983), "Follicle–stimulating Hormone Regulation of A–kinase Anchoring Proteins in Granulosa Cells*".
Carr, et al., *J.Biol.Chem.* 266:14188–14192 (1991), "Interaction of the Regulatory Subunit (RII) of cAMP–dependent Protein Kinase with RII–anchoring Proteins Occurs through an Amphipathic Helix Binding Motif*".
Carr and Scott, *T.I.B.S.* 17:246–249 (1992), "Blotting and band–shifting: techniques for studying protein–protein interactions".
Cheley, et al., *J.Biol.Chem.* 269:2911–2920 (1994), "Type II Regulatory Subunits of cAMP–dependent Protein Kinase and Their Binding Proteins in the Nervous System of *Aplysia californiac*\*".
Clipstone and Crabtree, *Nature* 357:695–697 (1992), "Identification of calcineurin as a key signalling enzyme in T–lymphocyte activation".
Coghlan, et al., *J.Biol.Chem.* 269:7658–7665 (1994), "Cloning and Characterization of AKAP 95, a Nuclear Protein That Associates with the Regulatory Subunit of Type II cAMP–dependent Protein Kinase*".
Coghlan, et al., *Mol.Cell.Biochem.* 127:309–319 (1993), "A–Kinase Anchoring Proteins: a key to selective activation of cAMP–responsive events?".
Cyert and Thorner, *J.Cell.Biol.* 107:841a (1989), "Calcineurin–like Activity in *Saccharomyces cerevisiae*".
de Groen, et al., *N.Eng.J.Med.* 317:861–866 (1987), "Central Nervous System Toxicity After Liver Transplantation".
DeCamilli, et al, *J.Cell.Biol.* 103:189–203 (1986), "Heterogeneous Distribution of the cAMP Receptor Protein RII in the Nervous System: Evidence for Its Intracellular Accumulation of Microtubules, Microtubule–organizing Centers, and in the Area of the Golgi Complex".
Deeg, et al., *Blood* 65:1325–1334 (1985), "Cyclosporine as Prophylaxis for Graft–Versus–Host Disease: A Randomized Study in Patients Undergoing Marrow Transplantation for Acute Nonlymphoblastic Leukemia".
Durfee, et al., *Genes and Development* 7:555–567 (1993), "The retinoblastoma protein associates with the protein phosphatase type 1 catalytic subunit".
Eichholtz, et al., *J.Biol.Chem* 268:1982–1986 (1993), "A Myristoylated Pseudosubstrate Peptide, a Novel Protein Kinase C Inhibitor*".
Eidelman, et al., *Transplnt.Proc.* 23:3175–3178 (1991), "Neurologic Complications of FK 506".
Ellis, et al., *JAMA* 256:3110–3116 (1986), "Cyclosporine Improves Psoriasis in a Double–blind Study".
Forre, et al., *Arthritis Reheum.* 30:88–92 (1987), "An Open, Controlled, Randomized Comparison Of Cyclosporine And Azahioprine In The Treatment Of Rheumatoid Arthritis: A preliminary Report".

(List continued on next page.)

*Primary Examiner*—Toni R. Scheiner
*Assistant Examiner*—Sheela J. Huff
*Attorney, Agent, or Firm*—Marshall, O'Toole, Gerstein, Murray & Borun

[57] ABSTRACT

The present invention provides compositions and methods useful for isolating calcineurin as well as inhibiting calcineurin activity. The compositions are peptides that contain regions that are homologous to calcineurin-binding regions of AKAP 79. Also provided are methods for determining if a cell contains a calcineurin-binding and PKA-binding anchoring protein that are useful for identifying additional proteins that bind both calcineurin and PKA.

1 Claim, 4 Drawing Sheets

OTHER PUBLICATIONS

Feutren, et al, *Lancet* 2:119–124 (1986), "Cyclosporin Increases The Rate And Length Of Remissions In Insulin–Dependent Diabetes Of Recent Onset".

Fung, et al., *Transplant.Proc.* 23:3105–3108 (1991), "Adverse Effects Associated With the Use of FK 506".

Glantz et al., *J.Biol.Chem.* 268:12796–12804 (1993), "Characterization of Distinct Tethering and Intracellular Targeting Domains in AKAP75 a Protein That Links cAMP–dependent Protein Kinase IIβ to the Cytoskeleton".

Glantz, et al. *Mol.Cell.Biol.* 3:1215–1228 (1992), "cAMP Signaling in Neurons: Patterns of Neuronal Expression and Intracellular Localization for a Novel Protein, AKAP 150, that Anchors the Regulatory Subunit of cAMP–Dependent Protein Kinase IIβ".

Greengard, et al., *Science* 253:1135–1138 (1991), "Enhancement of the Glutamate Response by a cAMP–Dependent Protein Kinase in Hippocampal Neurons".

Guerini and Klee, *Proc.Natl.Acad.Sci.* (USA) 86:9183–9187 (1989), "Cloning of human calcineurin A: Evidence for two isozymes and identification of a polyproline structural domain".

Harlow and Lane, *Antibodies:A Laboratory Manual*, Harlow and Lane (eds.), Cold Spring Harbor Laboratory:Cold Spring Harbor, NY (1988), pp. 313–318, "Immunoaffinity Purification of Antobodies on an Antigen Column".

Hashimoto, et al., *J.Biol.Chem.* 265:1924–1927 (1990), "Identification of an Autoinhibitory Domain in Calcineurin*".

Hathaway, et al., *J.Biol.Chem.* 265:8183–8189 (1981), "Interaction of Calmodulin with Myosin Light Chain Kinase and cAMP–dependent protein Kinase in Bovine Brain*".

Hausken, et al., *J.Biol.Chem.* 269:24245–24251 (1994), "Type II Regulatory Subunit (RII) of the cAMP–dependent Protein Kinase Interaction with A–kinase Anchor Proteins Requires Isoleucines 3 and 5*".

Hirsch, et al., *J.Biol.Chem.* 267:2131–2134 (1992), "Cloning and Expression of an Intro–less Gene for AKAP 75, an Anchor Protein for the Regulatory Subunit of cAMP–dependent Protein Kinase IIβ*".

Hubbard and Cohen, *T.I.B.S.* 17:172–177 (1993), "On target with a new mechanism for the regulation of protein phosphorylation".

Jain, et al., *Nature* 365:352–355 (1993), "The T–cell transcription factor $NFAT_p$ is a substrate for calcineurin and interacts with Fos and Jun".

Kahan, et al, *Transplatation* 43:197–204 (1987), "Complications of Cyclosporine–Prednisone Immunosuppression in 402 Renal Allograft Recipients Exclusively Followed At a Single Center For From One To Five Years".

Kahan, *N.Eng.J.Med.* 321:1725–1738 (1989), "Cyclosporine".

Keegan, et al., *Science* 231:699–704 (1986), "Separation of DNA Binding from the Transcription–Activating Function of a Eukaryotic Regulatory Protein".

Keryer et al., *Exp.Cell Res.* 204:230–240 (1993), "A High–Affinity Binding Protein for the Regulatory Subunit of cAMP–Dependent Protein Kinase II in the Centrosome of Human Cells".

Klee, et al. *Adv.Enzymol.* 61:149–200 (1984), "Calcineurin".

Ma and Ptashne, *Cell* 48:847–853 (1987), "Deletion Analysis of GAL4 Defines Two Transcriptional Activating Segments".

Mason, *Pharmacol.Rev.*, 42:423–434 (1989), "Pharmacology of Cyclosporine (Sandimmune) VII. Pathophysiology and Toxicology of Cyclosporine in Humans and Animals".

McCauley, et al., *Curr.Opin.Nephrol.Hyperten.* 2:662–669 (1993), "The nephrotoxicity of FK506 as compared with cyclosporine".

Morris, *J.Heart and Lung Transplant.* (Nov./Dec.) pp. S275–S285 (1993), "New Small Molecule Immunosuppressants for Transplantation: Review of Essential Concepts".

Najarian, et al., *Ann.Surg.* 201:142–157 (1985), "A Single Institution, Randomized, Prospective Trial of Cyclosporine Versus Azathioprine–Antilymphocyte Globulin for Immunosuppriession in Renal Allograft Recipients".

New York Hospital–Cornall Medical Center, *Curr.Opin.Immunol.* 6:784–790 (1994), "Which way for drug–mediated immunosuppression?".

Nussenblatt, et al., *Am.J.Ophthalmol.* 96:275–282 (1983), "Cyclosporin A Therapy in the Treatment of Intraocular Inflammatory Disease Resistant to Systemic Corticosteroids and Cytotoxic Agents".

O'Keefe, et al.,*Nature* 357:692–694 (1992), "FK–506–and CsA–sensitive activationof the interleukin–2 promoter by calcineurin".

Obar, et al., *Neuron* 3:639–645 (1989), "The RII Subunit of cAMP–Dependent Protein Kinase Binds to a Common Amino–Terminal Domain in Microtubule–Associated Proteins 2A, 2B, and 2C".

Oyer, et al., *Transplant Proc.* 15:Supp 1:2546–2552 (1983), "Cyclosporine in Cardiac Transplantation: A 2½ Year Follow–Up".

Perrino, et al, *J. Biol. Chem.* 267:15965–15969 (1992), "Characterization of the Phosphatase Activity of a Baculovirus–expressed Calcineurin A Isoform*".

Peters, et al., *Drugs* 4:746–794 (1993), "Tacrolimus A review of its Pharmacology, and Therapeutic Potential in hepatic and Renal Transplantation".

Rios, et al., *EMBO J.* 11:1723–1731 (1992), "Identification of a high affinity binding protein for the regulatory subunit RIIβ of cAMP–dependent protein kinase in Golgi enriched membranes of human lymphoblasts".

Rosenmund, et al., *Nature* 368:853–856 (1994), "Anchoring of protein kinase A is required for modulation of AMPA/kainate receptors on hippocampal neurons".

Ryffel, *Pharm.Rev.* 41:407–422 (1989), "Pharmacology of Cyclosporine VI. Cellular Activation: Regulation of Intracellular Events by Cyclosporine".

Schreiber, *Science* 251:283–287 (1991), "Chemistry and Biology of the Immunophilins and Their Immunosuppressive Ligands".

Schreiber and Crabtree, *Immunol. Today* 13:136–142 (1992), "The mechanism of action of cyclosporin A and FK506".

Scott, et al., *Proc.Natl.Acad.Sci.* (USA) 82:4379–4383 (1985), "Identifiation of an inhibitory region of the heat–stable protein inhibitor of the cAMP–dependent protein kinase".

Scott and Carr, *N.I.P.S.* 7:143–148 (1992), "Subcellular Localization of the Type II cAMP–Dependent Protein Kinase".

Scott and McCartney, *Mol. Endocrinol.* 8:5–11 (1994), "Localization of A–kinase through Anchoring Proteins".

Showstack, et al., *N.Eng.J.Med.* 321:1086–1092 (1989), "The Effect of Cyclosporine of the Use of Hospital Resources for Kidney Transplantation".

Skålhegg, et al., Science 263:84–87 (1994), "Location of cAMP–Dependent Protein Kinase Type with the TCR–CD3 Complex".

Spencer, et al., Science 262:1019–1024 (1993), "Controlling Signal Transduction with Synthetic Ligands".

Starzl, et al., N.Eng.J.Med. 305:266–269 (1981), "Liver Transplantation With Use of Cyclosporin A and Prednisone".

Stewart and Young, Solid Phase Peptide Synthesis, 2nd Edition, "Laboratory Techniques in Solid Phase Peptide Synthesis".

Stofko–Hahn, F.E.B.S. Letts. 302:274–278 (1992), "A single step purification for recombinant proteins, Characterization of a microtubule associated protein (MAP 2) fragment which associates with the type II cAMP–dependent protein kinase".

Tam, et al., J.Am.Chem.Soc. 105:6442–6455 (1983), "$S_N2$ Deprotection of Synthetic Peptides with a Low Concentration of HF in Dimethyl Sulfide: Evidence and Application in Peptide Synthesis[1]".

Tejani, et al., Kidney Intl. 29:206 (1986), "Cyclosporine (CY) Induced Remission of Relapsing Nephrotic Syndrome (RNS) In Children".

Thomson and Starlz, Immunol.Rev. 136:71–98 (1993), "New Immunosuppressive Drugs: Mechanistic Insights and Potential Therapeutic Advances".

Threurkauf and Vallee, J.Biol.Chem. 257:3284–3290 (1982), "Molecular Characterization of the cAMP–dependent Protein Kinase Bound to Microtubule–associated Protein 2*".

Toronto Lung Transplant, JAMA 259:2258–2262 (1988), "Experience With Single–Lung Transplantation for Pulmonary Fibrosis".

Wang, et al., Science 253:1132–1135 (1991), "Regulation of Kainate Receptors by cAMP–Dependent Protein Kinase and Phosphatases".

Weiss and Littman Cell 76:263–274 (1994), "Signal Transduction by Lymphocyte Antigen Receptors".

Rubino, et al., Neuron 3:631–638 (1989), "Localization and Characterization of the Binding Site for the Regulation Subunit of Type II cAMP–Dependent Protein Kinase on MAP2".

| | | |
|---|---|---|
| Mu clone 11.1 | ---------- PPPPPPPPPP GADRVVKAV PFPPTHRLTS EEVFD DGIP | 40 |
| Hu Calcineurin A1 | MAAPEPARAA PPPPPPPPPP GADRVVKAV PFPPTHRLTS EEVFD DGIP | 50 |
| Mu clone 11.1 | RVDVLKNHLV KEGRVDEEIA LRIINEGAAI LRREKTMIEV EAPITVCGDI | 90 |
| Hu Calcineurin A1 | RVDVLKNHLV KEGRVDEEIA LRIINEGAAI LRREKTMIEV EAPITVCGDI | 100 |
| Mu clone 11.1 | HGQFFDLMKL FEVGGSPANT RYLFLGDYVD RGYFSIE VL ---------- | 130 |
| Hu Calcineurin A1 | HGQFFDLMKL FEVGGSPANT RYLFLGDYVD RGYFSIE VL GTEDISINPH | 150 |
| Mu clone 11.1 | -------- YL WVLKILYPST LFLLRGNHEC RHLTEYFTFK QECKIKYSER | 172 |
| Hu Calcineurin A1 | NNINECVI YL WVLKILYPST LFLLRGNHEC RHLTEYFTFK QECKIKYSER | 200 |
| Mu clone 11.1 | VYEACMEAFD SLPLAALLNQ QFLCVHGGLS PEIHTLDDIR RLDRFKEPPA | 222 |
| Hu Calcineurin A1 | VYEACMEAFD SLPLAALLNQ QFLCVHGGLS PEIHTLDDIR RLDRFKEPPA | 250 |
| Mu clone 11.1 | FGPMCDLLWS DPSEDFGNEK SQEHFSHNTV RGCSYFYNYP AVCEFLQNNN | 272 |
| Hu Calcineurin A1 | FGPMCDLLWS DPSEDFGNEK SQEHFSHNTV RGCSYFYNYP AVCEFLQNNN | 300 |
| Mu clone 11.1 | LLSIIRAHEA QDAGYRMYRK SQTTGFPSLI TIFSAPNYLD VYNNKAAVLK | 322 |
| Hu Calcineurin A1 | LLSIIRAHEA QDAGYRMYRK SQTTGFPSLI TIFSAPNYLD VYNNKAAVLK | 350 |
| Mu clone 11.1 | YENNVMNIRQ FNCSPHPYWL PNFMDVFTWS LPFVGEKVTE MLVNVLSICS | 372 |
| Hu Calcineurin A1 | YENNVMNIRQ FNCSPHPYWL PNFMDVFTWS LPFVGEKVTE MLVNVLSICS | 400 |
| Mu clone 11.1 | DDELMTEGED QFD GSAAAR KEIIRNKIRA IGKMARVFSV LREESESVLT | 422 |
| Hu Calcineurin A1 | DDELMTEGED QFD GSAAAR KEIIRNKIRA IGKMARVFSV LREESESVLT | 449 |
| Mu clone 11.1 | LKGLTPTGML PSGVLAGGRQ TLQSGNDVMQ LAVPQMDWGT HSFANN HN | 472 |
| Hu Calcineurin A1 | LKGLTPTGML PSGVLAGGRQ TLQSGNDVMQ LAVPQMDWGT HSFANN SHN | 499 |
| Mu clone 11.1 | ACRE LLL FS SCLSS | 487 |
| Hu Calcineurin A1 | ACRE LLI FS SCLSS | 514 |

FIG. 3

CALCINEURIN INHIBITORY COMPOUNDS AND ANCHORING PROTEIN

This is a divisional application of U.S. patent application Ser. No. 08/344,227, filed Nov. 23, 1994, which is pending.

FIELD OF THE INVENTION

The present invention relates generally to regulation of the phosphatase enzymatic activity of calcineurin. More particularly, the present invention relates to inhibition of calcineurin's phosphatase activity by certain peptides.

BACKGROUND OF THE INVENTION

Calcineurin is a $Ca^{2+}$/calmodulin-dependent protein phosphatase and is an element of many intracellular signaling pathways. Guerini and Klee, *Proc. Natl. Acad. Sci. USA* 86:9183–9187 (1989). The protein has been identified in eukaryotic cells ranging from yeast to mammals. Cyert and Thorner, *J. Cell. Biol.*, 107:841a (1989) and Klee et al., *Adv. Enzymol.*, 61:149–200 (1984). Because calcineurin may affect many signaling pathways in the same cell, some means of specific targeting of calcineurin's activity is required. One cellular means for specifically targeting enzyme activity in a cell is by compartmentalization. Compartmentalization provides a means for segregation of signaling pathways and contributes to the specificity of cellular responses to different stimuli. Compartmentalization of certain enzymes occurs by interaction of the enzymes with specific anchoring proteins. For example, cAMP-dependent protein kinase (PKA) is anchored at specific intracellular sites by binding to A-Kinase Anchor Proteins (AKAPs). Hirsch et al., *J. Biol. Chem.*, 267:2131–2134 (1992). cAMP activates PKA by binding to the regulatory subunits (R) of the dormant PKA holoenzyme and causes the release of the active catalytic subunit (C). Two classes of R subunit exist; RI and RII which form the type I and type II PKA holoenzymes, respectively. The subcellular distributions of these PKA isoforms appear to be distinct. The RI isoforms (RIα and RI§) are reported to be predominantly cytoplasmic and are excluded from the nuclear compartment, whereas up to 75% of the RII isoforms (RIIα or RII§) are particulate and associated with either the plasma membrane, cytoskeletal components, secretory granules, the golgi apparatus, centrosomes or possibly nuclei.

AKAPs have been identified in a variety of organisms. At least 7 proteins that bind the regulatory subunit of PKA in *Aplysia californica*, a marine invertebrate have been identified. Cheley et al., *J. Biol. Chem.*, 269:2911–2920 (1994). One of these proteins is enriched in crude membrane fractions and taxol-stabilized microtubules and may thus anchor microtubules to the cell membrane as well as bind PICA. A mammalian AKAP has been identified that is related to microtubules; microtubule-associated protein 2 (MAP2) attaches PKA to the cytoskeleton. Threurkauf and Vallee, *J. Biol. Chem.*, 257:3284–3290 (1982) and DeCamilli et al., *J. Cell Biol.*, 103:189–203 (1986). The PKA-binding site on MAP2 is a 31-residue peptide in the amino-terminal region of the molecule. Rubino et al., *Neuron*, 3:631–638 (1989) and Obar et al., *Neuron*, 3:639–645 (1989).

Another AKAP that associates with microtubules, AKAP 150, accumulates in dendrites in close association with microtubules. Glantz et al., *Mol. Biol. Cell*, 3:1215–1228 (1992). AKAP 150 is present in several neuronal cell types and is a member of a family of AKAPs that are the principal AKAPs from mammalian brains. Other members of this family include AKAP 75 found in bovine brain and AKAP 79 found in human brain. Glantz et al., *J. Biol. Chem.*, 268:12796–12804 (1993). AKAP 75 apparently binds cytoskeletal elements through two non-contiguous regions near the N-terminus of AKAP 75. AKAP 79 is predominantly present in postsynaptic densities (PSDs) in the human forebrain. Carr et al., *J. Biol. Chem.*, 267:16816–16823 (1992). Inhibition of binding between AKAP 79 and PKA in hippocampal neurons has been shown to inhibit alpha-amino-3-hydroxy-5-methyl-4-isoxazole propionic acid/kainate glutamate receptors. Rosenmund et al., *Nature*, 368:853–856 (1994).

Other AKAPs have also been characterized. Exposure of granulosa cells to follicle-stimulating hormone and estradiol has been demonstrated to up-regulate expression of an 80 kDa AKAP. Carr et al., *J. Biol. Chem.*, 268:20729–20732 (1993). Another AKAP, Ht31, has been cloned from a human thyroid cDNA library. Carr et al., *J. Biol. Chem.*, 267:13376–13382 (1992). Another AKAP, AKAP 95, changes its intracellular location during the cell cycle. AKAP 95 is an integral nuclear protein during interphase, but becomes associated with cytoplasmic PKA when the nuclear membrane breaks down during mitosis. This suggests that AKAP 95 could play a role in targeting activity of certain isoforms of PKA during cAMP-responsive events linked to the cell cycle. Coghlan et al., *J. Biol. Chem.*, 269:7658–7665 (1994). Other known AKAPs include an 85 kDa AKAP which links PKA to the Golgi apparatus (Rios et al., *EMBO J.*, 11:1723–1731 (1992)) and a 350 kDa AKAP that binds PKA to centromeres (Keryer et al., *Exp. Cell Res.*, 204:230–240 (1993)).

The known AKAPs share a common PKA-binding feature. Although the primary structure of the AKAPs is not conserved, each has a secondary structure motif that includes an amphipathic helix region. Scott and McCartney, *Mol. Endo.*, 8:5–11 (1994). Binding of AKAPs to the regulatory subunit of PKA is blocked by a peptide that mimics this helical structure of the PKA binding region of AKAPs. Disruption of the peptide's helical structure by an amino acid substitution abolishes the PKA-AKAP binding block (Carr et al., *J. Biol. Chem.*, 266:14188–14192 (1991)), demonstrating that PKA binding occurs in the amphipathic helix of AKAPs and is governed by the secondary structure of the AKAP molecules. This provides a means for segregation of a kinase that, like calcineurin, is common to many signaling pathways yet may act in a pathway-specific manner.

One specific action of calcineurin is participation in T cell activation. Clipstone and Crabtree, *Nature*, 357:695–697 (1992) and O'Keefe et al., *Nature*, 357:692–694 (1992). In T cells, calcineurin participates in regulation of IL-2 expression following T cell stimulation. Weiss and Littman, *Cell*, 76:263–274 (1994). Nuclear factor of activated T cells ($NFAT_p$) has been shown to be a substrate for calcineurin phosphatase activity. It has been suggested that, following T cell stimulation, calcineurin-mediated $NFAT_p$ dephosphorylation allows translocation of $NFAT_p$ from the cytoplasm to the nucleus where $NFAT_p$ interacts with Fos and Jun to induce expression of the IL-2 gene. Jain et al., *Nature*, 365:352–355 (1993).

Calcineurin's role in T cell activation provides a target for therapeutic intervention into T cell-mediated disorders and medications have been developed that inhibit calcineurin. Two calcineurin-inhibiting drugs, cyclosporin A (cyclosporin) and FK506, have been used in the clinic. Thomson and Starzl, *Immunol. Rev.*, 136:71–98 (1993). Both cyclosporin and FK506 inhibit calcineurin only after binding to distinct intracellular proteins known as immunophilins (cyclophilin and FKBP 12, respectively). Schreiber and Crabtree, *Immunology Today*, 13:136–142 (1992). Thus, cyclosporin and FK506 act as prodrugs. Following binding to their respective immunophilins, the drug/immunophilin complexes bind calcineurin, thereby inhibiting the phosphatase activity.

Calcineurin inhibition has been most effectively exploited in the treatment of graft rejection following organ transplant. Cyclosporin and FK506 have been employed following renal, hepatic, cardiac, lung, and bone marrow transplants. The Canadian Multicentre Transplant Study Group, *N. Engl. J. Med.*, 314:1219–1225 (1986); Oyer et al., *Transplant Proc.*, 15:Suppl 1:2546–2552 (1983); Starzl et al., *N. Engl. J. Med.*, 305:266–269 (1981); The Toronto Lung Transplant Group, *JAMA*, 259:2258–2262 (1988); and Deeg et al., *Blood*, 65:1325–1334 (1985). The use of these medications has significantly prolonged graft survival and lessened morbidity following transplant. Najarian et al., *Ann. Surg.*, 201:142–157 (1985) and Showstack et al., *N. Engl. J. Med.*, 321:1086–1092 (1989).

Cyclosporin also has been used in a variety of autoimmune-related diseases. Uveitis generally improves within a few weeks of therapy, but quickly relapses after cyclosporin is discontinued. Nussenblatt et al., *Am J. Ophthalmol.*, 96:275–282 (1983). Similarly, psoriasis generally improves with cyclosporin therapy, but quickly relapses after treatment. Ellis et al., *JAMA*, 256:3110–3116 (1986). "Honeymoon" periods of insulin independence may be induced and prolonged in both new onset Type I and Type II diabetes mellitus when cyclosporin is administered within two months of insulin therapy. Feutren et al., *Lancet*, 2:119–124 (1986) and Bougneres et al., *N. Engl. J. Med.*, 318:663–670 (1988). A variety of nephropathies, including minimal-change focal and segmental, membranous, and IgA-mediated nephropathies, may also be sensitive to cyclosporin, although observed reductions in proteinuria may be due to a decrease in the glomerular filtration rate and not healing of the basement membrane. Tejani et al., *Kidney Intl.*, 29:206 (1986). Cyclosporin administration also has a dose-dependent effect on rheumatoid arthritis, although such treatment is associated with a high incidence of nephrotoxicity. Førre et al., *Arthritis Rheum.*, 30:88–92 (1987).

As mentioned above, cyclosporin has been associated with nephrotoxicity. Mason, *Pharmacol. Rev.*, 42:423–434 (1989). Depressed renal function occurs in virtually all patients treated with cyclosporin. Kahan, *N. Engl. J. Med.*, 321:1725–1738 (1989). This can generally be reversed by cessation of cyclosporin therapy. Unfortunately, in organ graft recipients substitution of other commonly used immunosuppressives for cyclosporin carries a high risk of graft rejection. In renal transplant patients this can require reinstitution of dialysis. In patients that have received hearts, lungs, or livers, graft rejection can be fatal. Although less common than nephrotoxicity, neurotoxicity and hepatotoxicity are also associated with cyclosporin therapy. de Groen et al., *N. Engl. J. Med.*, 317:861–866 (1987) and Kahan et al., *Transplantation*, 43:197–204 (1987).

Although there is less clinical experience, significant toxicity has also become apparent in the use of FK506. Like cyclosporin, FK506 is associated with significant nephrotoxicity. Peters et al., *Drugs*, 4:746–794 (1993). The clinical presentation, lesion morphology, and incidence are approximately equivalent to those of cyclosporin. McCauley, *Curr. Op. Nephrol. Hyperten.*, 2:662–669 (1993). Neurotoxicity has also been associated with FK506. Eidelman et al., *Transplant. Proc.*, 23:3175–3178 (1991) and Fung et al., *Transplant. Proc.*, 23:3105–3108 (1991). In contrast to cyclosporin, FK506 has a hepatotrophic, rather than hepatotoxic, effect. Peters et al., supra.

In view of the significant potential toxicity of immunosuppressive agents, such as cyclosporin and FK506, it is clear that there is a need in the art for additional agents that inhibit calcineurin. These agents would preferably be associated with fewer toxic side effects than presently available agents and thus could provide an advance in immunosuppressive therapy.

SUMMARY OF THE INVENTION

The present invention is based, in part, on the discovery that calcineurin binds AKAP 79. By binding both PKA and calcineurin, AKAP 79 co-localizes a kinase and a phosphatase that may regulate flux through a specific signaling pathway. The present invention accordingly provides compositions and methods for isolating calcineurin as well as for inhibiting calcineurin activity in a cell. The isolation methods comprise contacting a cellular fraction with AKAP 79 or a calcineurin-binding fragment thereof which has been immobilized to a solid substrateand then elutin calcineurin therefrom. The calcineurin inhibiting methods comprise contacting the cell with AKAP 79 or a calcineurin-binding fragment peptide thereof. Preferrably, the calcineurin-binding peptide does not also bind PKA. Preferred peptides comprise the following amino acid sequence:

Arg-Arg-Lys-Arg-Ser-Gln-Ser-Ser-Lys-Glu-Glu-Lys-Pro                            (SEQ ID NO:1).

Alternative peptides useful in the practice of the calcineurin inhibiting methods of the present invention include:

Arg-Arg-Lys-Arg-Ser-Gln-Ser-Ser-Lys-Glu-Glu-Lys-Pro-Leu-Gln                   (SEQ ID NO:2)

and

Arg-Arg-Lys-Arg-Ser-Gln-Ser-Ser-Lys-Glu-Glu-Lys-Pro-Phe-Lys                   (SEQ ID NO:3).

These peptides are homologous to amino acid sequences of AKAP 79 that bind calcineurin. Although the peptides are similar to the calcineurin binding region of FKBP12, unlike calcineurin inhibition by the FK506/FKBP12 complex, the peptides inhibit calcineurin activity without requiring interaction with another molecule.

The peptides may be modified to facilitate passage into the cell, such as by conjugation to a lipid soluble moiety. For example, the peptides may be conjugated to myristic acid. Alternatively, the peptides may be packaged in liposomes that may fuse with cell membranes and release the peptides into the cells.

Another aspect of the present invention are methods for determining if a cell contains a calcineurin-binding and PKA-binding anchoring protein. The methods generally comprise lysing the cell to form a lysate; incubating the lysate with a solid support, which solid support has calcineurin molecules immobilized thereon; washing the lysate from the solid support; contacting the solid support with a labeled PKA regulatory subunit, washing unbound regulatory subunit from the solid support; detecting label remaining on the solid support; and determining therefrom the presence of a calcineurin-binding and PKA-binding anchoring protein in the cell. Alternatively, the PKA regulatory subunit may immobilized on the solid support and calcineurin may be the labeled molecule. Generally, the PKA regulatory subunit will be an RII subunit.

These methods are useful for identifying additional proteins that bind both PKA and calcineurin. Identification of other such proteins may provide tissue specific targets for therapeutic intervention.

Also comprehended by the present invention are methods for identifying compounds that modulate binding between calcineurin and a calcineurin anchoring protein. Either calcineurin or the anchoring protein may be bound to a solid substrate. The unbound binding partner is detectably labeled. The binding partners are incubated in the presence of a test compound. The effect of the test compound on binding between calcineurin and the calcineurin anchoring protein is determined by observing the amount of label bound to the immoblized binding partner. A reduction in the amount of label bound in the presence of the test compound compared to the amount of label bound in the absence of the test compound indicates that the test compound is an inhibitor of binding between calcineurin and the calcineurin anchoring protein. Other assays, such as scintillation proximity assays may also be employed.

BRIEF DESCRIPTION OF THE FIGURES

FIG. 3 illustrates homology between clone 11.1 and human calcineurin isoform 11.1.

DETAILED DESCRIPTION OF THE INVENTION

Figure 1A:
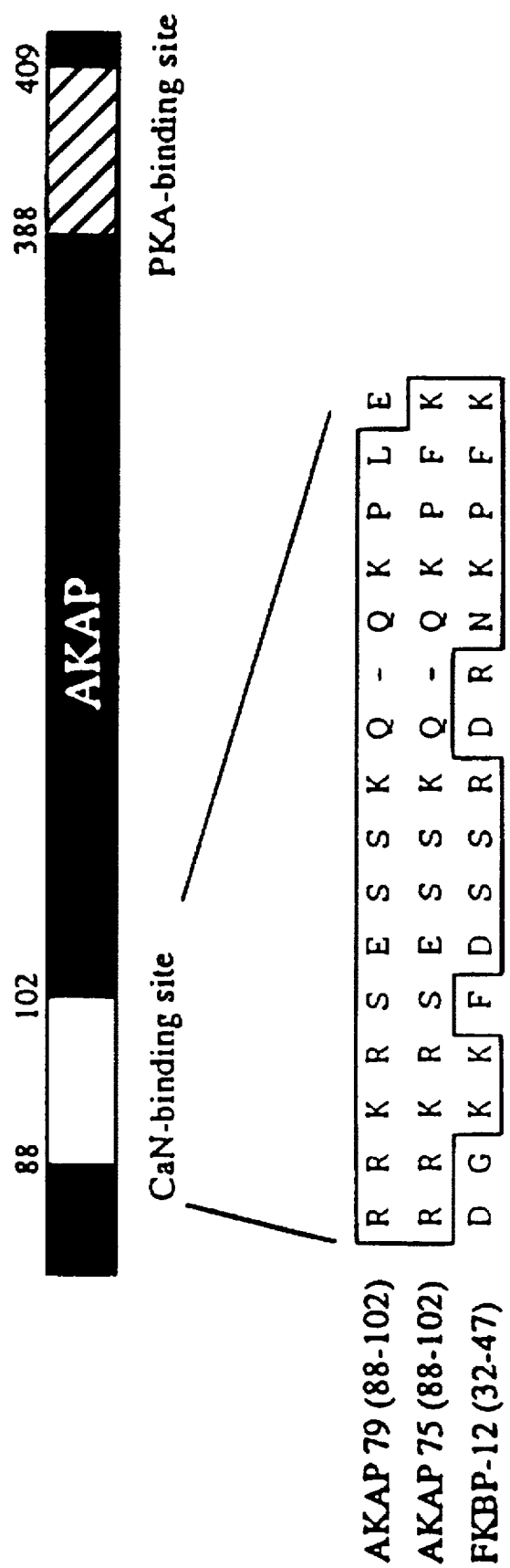
FIGS. 1(a–c) illustrate inhibition of calcineurin phosphatase activity by full-length AKAP 79 and a calcineurin-binding fragment of AKAP 79.

The peptides employed in the methods of the present invention may be synthesized in solution or on a solid support in accordance with conventional techniques as described in Stewart and Young, Solid Phase Peptide Synthesis, 2nd ed., Pierce Chemical Company, (1984) or Tam et al., J. Am. Chem. Soc., 105:6442 (1983), both of which are incorporated herein by reference. The peptides may be myristoylated by standard techniques as described in Eichholtz et al., J. Biol. Chem., 268:1982–1986 (1993), incorporated herein by reference. Encapsulation of the peptides in liposomes may also be performed by standard techniques as generally described in U.S. Pat. Nos. 4,766, 046; 5,169,637; 5,180,713; 5,185,154; 5,204,112; and 5,252, 263 and PCT Patent Application No. 92/02244, each of which is incorporated herein by reference.

The following examples are offered by way of illustration and not of limitation.

EXAMPLE 1

This example demonstrates the naturally-occurring association of calcineurin with AKAP 79 and PKA. AKAP 79 thus functions to co-localize both a ubiquitous kinase and ubiquitous phosphatase. This co-localization may provide for specific regulation of enzymes in signaling pathways through phosphorylation or dephosphorylation of the enzymes.

Immunoprecipitation of calcineurin (CaN) from a calmodulin-agarose purified bovine brain extract was achieved using affinity-purified antibodies specific for either CaN A or CaN B as generally described in Harlowe and Lane, Antibodies: A Laboratory Manual, Cold Spring Harbor Press, Cold Spring Harbor, N.Y. (1988), except a final wash using buffer A (10 mM HEPES pH 7.9, 1.5 mM MgCl, 10 mM KCl, 1 mM PMSF and 10 µM IBMX)+0.4M NaCl was included. PKA activity was measured as described in Scott et al., Proc. Natl. Acad. Sci. USA, 82:4379–4383 (1985), incorporated herein by reference, after elution of the immunoprecipitate with 0.1 mM cAMP. Phosphorylation of immunoprecipitated proteins was initiated by addition of 0.1 mM $^{32}$P-ATP ($1.5 \times 10^5$ cpm/nmol) and, after 30 min at 30° C., reactions were terminated by addition of SDS-loading buffer and subjected to SDS-PAGE. PKA R-subunit was purified from the 30–60% $(NH_4)_2SO_4$ fraction of brain extract using cAMP-agarose by the methods described in Coghlan et al., J. Biol. Chem., 269:7658–7665 (1994) (incorporated herein by reference), except protein was eluted with 0.5 mM Ht31 peptide (SEQ ID NO:4). Western blots and PKA RII overlays were performed as described in Coghlan et al., supra.

Kinase activity was detected in the calmodulin purified extract, was enriched 123±3.6 fold (±standard deviation; n=3) in the CaN immunoprecipitate, and was specifically inhibited by a peptide that inhibits PKA kinase activity. PKI peptide (SEQ ID NO:5), indicating that the catalytic (C) subunit of PKA was a component of the isolated complex. The bovine homologue of AKAP 79 (AKAP 75) and RII, both substrates for the C subunit, were also present in the immunoprecipitate and were phosphorylated upon addition of cAMP and $^{32}$P-ATP. In complementary experiments, R subunits of PICA were isolated from crude extracts of bovine brain by affinity chromatography on cAMP-agarose. Treatment of the affinity column with Ht31 peptide specifically eluted AKAP 75 from the cAMP-bound RII and also released both CaN A and B subunits. Approximately 5% of the total CaN present in the lysate was found to be associated with AKAP 75 and RII as detected on western blots. Combined, these results suggest simultaneous association of PKA and CaN with the AKAP.

EXAMPLE 2

This example demonstrates inhibition of calcineurin's phosphatase activity by peptides from AKAP 79.

To determine whether AKAP 79 peptide binding was inhibitory, calcineurin (CaN) activity was assayed in the presence of recombinant AKAP 79. Briefly, recombinant AKAP 79 was expressed in E. coli as described in Carr et al., J. Biol. Chem., 267:16816–16823 (1992), incorporated herein by reference. CaN and the constitutively active truncation mutant $CaN_{420}$ (a truncated, $Ca^{2+}$/calmodulin independent constitutively active form of CaN (Perrino et al., J. Biol. Chem., in press)) were expressed in Sf9 cells and purified on calmodulin-Sepharose as described in Perrino et al., J. Biol. Chem., 267:15965–15969 (1992), incorporated herein by reference. Phosphatase activity toward $^{32}$P RII peptide substrate was measured as described in Perrino et al., supra. CaN (30 nM), calmodulin (100 nM) and $^{32}$P RII peptide (22 µM) were incubated with AKAP 79 protein and AKAP 79 peptide (SEQ ID NO:1-amino acids 81–102) over the indicated range of concentrations indicated in FIG. 1B. Calmodulin was omitted from $CaN_{420}$ assays. $^{32}$P released from the substrate was measured in triplicate samples in three separate experiments by scintillation counting. The inhibition constant ($K_i$) of recombinant AKAP 79 for CaN was determined by linear regression analysis of data. $K_i$ values for AKAP 79 peptide were estimated by determining the $IC_{50}$ using a fixed substrate concentration at $K_m$ (42 µM).

Figure 1B:
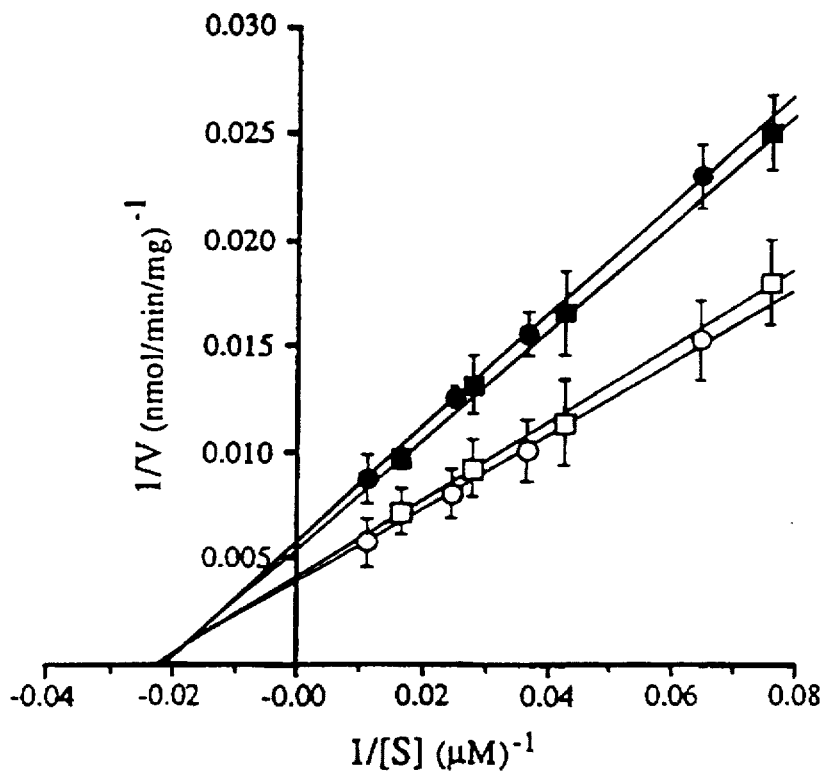
Figure 1C:
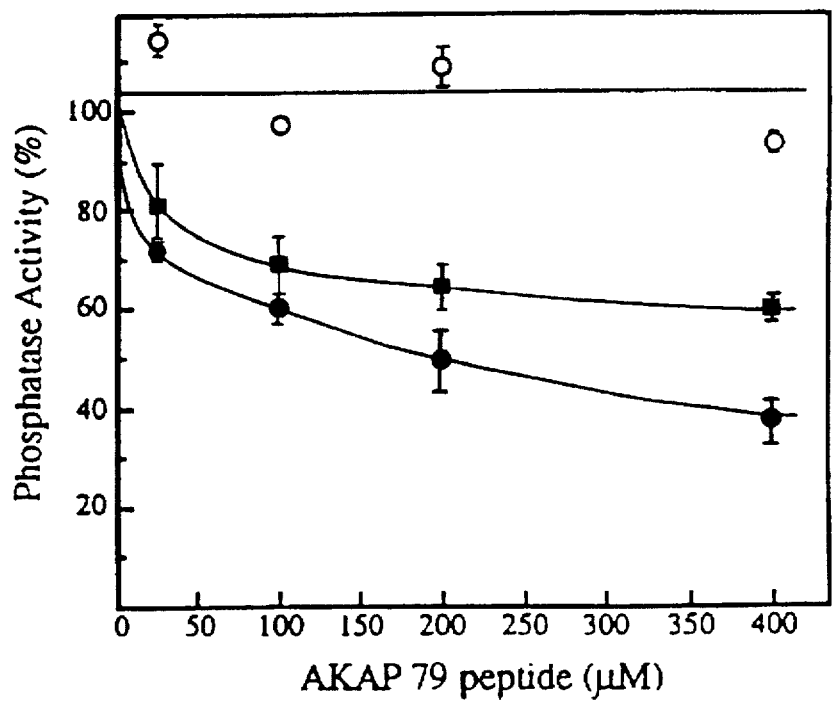

FIG. 1A illustrates a Lineweaver-Burk plot of AKAP 79 inhibition of both full-length CaN ($Ca^{2+}$/calmodulin dependent) (circles) and CaN$_{420}$ (squares) in a non-competitive manner with respect to phosphorylated RII peptide substrate. The open symbols represent phosphatase activity in the absence of AKAP 79 and the fried symbols represent phosphatase activity in the presence of AKAP 79. The synthetic peptide corresponding to the AKAP 79 peptide inhibited both full-length CaN (filled circles) and CaN$_{420}$, whereas the Ht31 peptide was not an inhibitor of CaN (FIG. 1B). The observed inhibition was specific for calcineurin; the AKAP 79 peptide did not significantly affect the activity of protein phosphatases 1 (open diamonds) or 2A (crosses) at peptide concentrations as high as 0.4 mM. Although CaN-binding sites on AKAP 79 and FKBP-12 are similar, their differences may have functional significance: FK506 (2 µM) did not affect the potency of inhibition and recombinant AKAP 79 did not display peptidyl prolyl isomerase activity toward a fluorescent peptide substrate. Further, the CaN B subunit which is required for FK506/FKBP interaction with the CaN A subunit is not required for interaction of AKAP 79 with the CaN A subunit. Also, while the FK506/FKBP interaction with CaN A is calcium/calmodulin dependent, the AKAP 79 inhibition of calcineurin activity is calcium/calmodulin independent. Collectively, these findings suggest that CaN in its inactive state is localized by AKAP 79 in a manner analogous to AKAP-bound PKA.

EXAMPLE 3

This example demonstrates subcellular distribution of type II PKA and calcineurin in tissue.

The subcellular location of many protein kinases and protein phosphatases is defined by association with targeting subunits. AKAP 79 represents a novel member of this class of regulatory proteins as it serves a bifunctional role in localizing both PKA and CaN.

Cells were cultured, formalin-fixed, and immunostained as described in Rosenmund et al., *Nature*, 368:853–856 (1994). FITC-conjugated anti-goat secondary antisera was used for RII staining. Biotinylated anti-rabbit secondary antisera and streptavidin-Texas-Red (Jackson) were used in staining for CaN. Images were obtained using a Biorad MRC-600 confocal laser scanning system (A1 and A2 filters) with a Nikon optiphot 2 microscope equipped with 60× planappo chromat (1.6 NA) oil immersion lens. Confocal sections were between 1.5 and 2 µm absolute thickness.

Figure 2A:
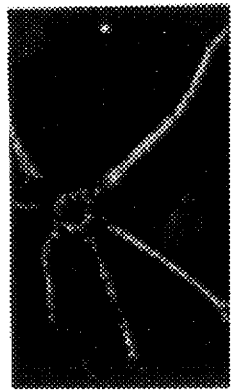
FIGS. 2(a–c) illustrate subcellular localization of type II PKA and calcineurin as well as the co-localization of type II PKA and calcineurin.
Figure 2B:
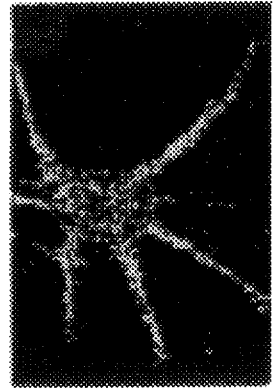
Figure 2C:
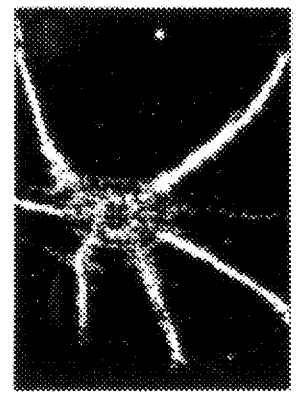

AKAP 79 homologues were observed in bovine, porcine, rabbit, and murine brain. This indicates that co-localization of PKA and CaN may be a universal phenomenon that adapts neurons for specific signal transduction events. Using immunocytochemical methods, the subcellular distribution of type II PKA and CaN was examined in cultured hippocampal neurons. The staining patterns for RII (green label in FIG. 2A) and CaN (red label in FIG. 2B) were regionally dispersed and overlapped in the neurites (RII is red and CaN is green in FIG. 2C). These findings are consistent with co-localization of type II PKA and CaN by the AKAP and suggest a role for the ternary complex in regulating synaptic transmission. This is consistent with experiments demonstrating co-localization of RII and AKAP 79 in these cells, and by studies showing that AKAP 79, type II PKA and CaN are components of postsynaptic densities. Potential substrates for the localized ternary transduction complex may include AMPA/kainate receptors, which are modulated by AKAP-targeted PKA.

EXAMPLE 4

This example demonstrates interaction between AKAP 79 and calcineurin in a yeast dihybrid assay. Employing AKAP 79 as the "bait", calcineurin encoded by cDNA from a murine T cell library was found to bind to AKAP79.

The assay was performed as generally described in Durfee, et al., *Genes and Development* 7:555–567 (1993), incorporated herein by reference. The "target" and "bait" were two plasmids, each containing part of the Gal-4 transcription factor. The "bait" plasmid (pAS1) was a 2 micron based plasmid with an ADH promoter linked to the Gal-4 DNA binding subunit [bp 1–147 as described in Keegan et al., *Science*, 231:699–704 (1986), incorporated herein by reference], followed by a hemagglutin (HA) tag, polyclonal site and an ADH terminator. Selection was maintained using SC-Trp media. The "target" construct was a leu2, 2 micron based plasmid containing an ADH promoter and terminator with the Gal-4 transcription activation domain II [amino acids 768–881 as described in Ma and Ptashne, *Cell*, 48:847–853 (1987), incorporated herein by reference] followed by a multiple cloning site. This vector, pACT, was utilized in the construction of a mouse T cell cDNA fusion library. *Saccharomyces cerevisiae* y190 used in the screening was designed with two reporter genes integrated into its genome. The reporter genes are under control of a Gal-1 promoter containing Gal-4 binding sites. If the proteins encoded by the bait plasmid and the target plasmid associate, the Gal-4 transcription factor subunits are brought together and function to initiate transcription of the reporter genes.

A 1.3 Kb NcoI/BamH1 fragment containing the coding region of AKAP 79 was isolated from a pET11d backbone and ligated to pAS1 to act as "bait" for the screen. One µg of this construct was transformed into y190 MATa and y190 MATα using a standard lithium acetate-PEG transformation protocol. Four isolates of each mating type (y190A pASI AKAP 79 1–4 and y190α pAS1 AKAP 79 1–4) were tested for their ability to interact with a fusion construct pACT-RII which contains the regulatory subunit (RII amino acids 1–89) of PKA. This was achieved by mating the strains on YEPD (1% Bacto-yeast extract, 2% Bacto-peptone, 2% dextrose, and 2% Bacto agar) overnight at 30° C. and then selecting for diploids on SC-Leu-Trp plates. The *E. coli* lac Z gene acting as the reporter could then be assayed for β-galactosidase activity. The mated strains were replicated to SC-Leu-Trp plates that had been overlayed with Hybond-N filters (Amersham) and grown overnight. The filters were placed in liquid nitrogen for one minute to crack open the yeast. A 3MM paper disc was saturated with approximately 3 ml 0.1% X-gal in 60 mM Na$_2$HPO$_4$, 40 mM NaH$_2$PO$_4$, 10 mM KCl and 10 mM MgSO$_4$. The lysed yeast filter was placed on top of the disc and allowed to develop at 30° C. for approximately 1–2 hours. Diploid strains containing both pAS1 AKAP 79 and pACT RII fusions that were positive for β-gal activity were indicated by mining the yeast patch a blue color. As a control, the bait AKAP 79 plasmid remained white when mated with an empty pACT control.

Detection of the Gal-4 AKAP 79 fusion protein was achieved by growing y190A AKAP 79 (isolates 1 and 2) and y190a AKAP 79 (isolates 1 and 2) to a density of 2×10$^7$ cells/ml in 50 ml SC-Trp media. Cells were pelleted at 3000×g for 10 minutes and lysed with 200 µl glass beads (size 425–600 microns) in 25 mM Tris pH8, 5 mM EDTA, 5 mM EGTA, 2 mM O-phenanthroline, 1 mM DTT, 25 µM AEBSF, 1 mM Benzanidine, 1 µg/ml PLACC (Pepstalin, Leupeptin, Aprotinin, Calpain I and ID, and 20 µg/ml Bestantin lysis buffer. Cells were alternately vortexed for one minute and iced for one minute for a total of 24 minutes (12 cycles). Protein concentrations were determined and 30 μg of total protein was loaded onto 10% SDS-PAGE gel. The gel was wet transferred to Immobilon-P (Millipore) and detected by standard procedures using an anti-HA monoclonal antibody 12CA5 (Bab Co., Berkeley, Calif.) and goat anti-mouse IgG alkaline phosphatase conjugated secondary antiserum (Biorad, Hercules, Calif.). A Gal-4 AKAP 79 fusion protein of approximately 100 kDa was readily detectable indicating the correct size product was present within these strains.

y190A pAS1 AKAP 79 isolate 1 was chosen to screen a pACT murine T cell cDNA library. A 500 ml SC-Trp culture ($OD_{600}$=0.6–0.8) was harvested, washed with 100 ml distilled water, and repelleted. The pellet was brought up in 50 ml LiSORB (100 mM lithium acetate, 10 mM Tris pH8, 1 mM EDTA pH8, and 1M Sorbitol), transferred to a 1 liter flask and shaken at 220 RPM for an incubation of 30 min at 30° C. The cells were then pelleted and resuspended with 625 μl LiSORB, and held on ice while preparing the DNA.

The DNA was prepared for transformation by boiling 400 μl 10 mg/ml Salmon sperm DNA for 10 min after which 500 μl LiSORB was added and allowed to slowly cool to room temperature. DNA from the Mu T cell library was added (40–50 μg) from a 1 mg/ml stock. The iced yeast culture was dispensed into 10 Eppendorf tubes with 120 μl of prepared DNA. The tubes were incubated at 30° C. at 220 RPM. After 30 minutes, 900 μl of 40% $PEG_{3350}$ in 100 mM Li acetate, 10 mM Tris pH 8 and 1 mM EDTA pH 8 was mixed with each culture and returned to incubate for an additional 30 min. The samples were then pooled and a small aliquot (5 μl) was removed to test for transformation efficiency and plated on SC-Leu-Trp plates. The remainder of the cells were added to 100 ml SC-Leu-Trp-His media and grown for 1 hr at 30° C. with shaking at 220 RPMS. Harvested cells were resuspended in 5.5 ml SC-Leu-Trp-His+50 mM 3AT (3-amino triazole) media and 300 μl aliquots plated on 150 mm SC-Leu-Trp-His+50mM 3AT and left to grow for 1 week at 30° C.

After four days, titer plates were counted and $1.1 \times 10^5$ colonies were screened. Large scale β-gal assays were performed on library plates and ten positive clones were isolated for single colonies. One of these colonies grew substantially larger than the rest, and was termed clone 11.1. Total yeast DNA was prepared from these strains and leu2 plasmid DNA was isolated. The "rescued" plasmid was used to retransform the original y190A pAS1 AKAP 79 bait strain and y190a. Only clone 11.1 remained positive for β-galactosidase activity in y190A pAS1 AKAP 79. y190a containing pACT clone 11.1 remained white serving as a negative control.

Restriction digestion with endonuclease Xho1 released a 2.3 Kb insert and the plasmid was sequenced in the forward and reverse directions. Reactions from the Dye Deoxy Terminator Cycle Sequencing Kit (Applied Biosystems, Inc. Foster City, Calif.) using symmetric polymerase chain reaction (PCR) on double stranded templates were analyzed on an ABI 373A automated sequencer (Applied Biosystems, Inc.). Sequence from clone 11.1 revealed an open reading frame 487 aa long (SEQ ID NO:6) which was correctly fused to the Gal-4 activation domain of pACT. The NIH sequence database was searched and the sequence was found to be closely homologous to the human calmodulin dependent protein phosphatase, calcineurin. Computer analysis between clone 11.1 and the human isoform A1 showed an 80% identity on the nucleic acid level and 93% identity on the amino acid level (FIG. 3). The first 10aa and an 18aa insert in the human sequence are not present in the mouse 11.1 sequence. Clone 11.1 is closely related to the mouse calcineurin A b sequence, but is distinctly dissimilar at the carboxy-terminus. Likewise the human calcineurin A1 and human calcineurin A2 isoforms are closely homologous but are distinct from each other at their 3' ends.

Specificity of the AKAP 79-calcineurin interaction was demonstrated by mating the calcineurin pACT containing strain with other unrelated bait strains. Crosses were performed as described above with strains containing pAS1 fused to RII (1–89), casein kinase 1, phosphodiesterase 32 (HDUN2) and AKAP Ht31. β-galactosidase activity was negative in all of these diploid strains.

All publications and patent applications mentioned in this specification are indicative of the level of skill of those skilled in the art to which the invention pertains. All publications, patents, and patent applications are herein incorporated by reference to the same extent as if each individual publication, patent, or patent application was specifically and individually indicated to be incorporated herein by reference.

Although the foregoing invention has been described in some detail by way of illustration and example for purposes of clarity of understanding, it is understood that certain changes and modifications are within the level of skill in the an and are within the scope of the appended claims.

---

What is claimed is:

1. A method for determining if a cell contains a calcineurin-binding and PKA-binding anchoring protein, the method comprising the steps of:

lysing the cell to form a lysate;

incubating the lysate with a solid support, the solid support having calcineurin molecules immobilized thereon;

washing the solid support;

contacting the solid support with a labeled PKA regulatory subunit that can bind an anchoring protein;

washing from the solid support regulatory subunit that did not bind;

detecting regulatory subunit remaining bound on the solid support; and determining therefrom the presence of a calcineurin-binding and PKA-binding protein in the cell.

* * * * *

UNITED STATES PATENT AND TRADEMARK OFFICE
CERTIFICATE OF CORRECTION

PATENT NO.   :   5,629,163

DATED   :   May 13, 1997

INVENTOR(S)   :   SCOTT, et al.

It is certified that error appears in the above-identified patent and that said Letters Patent is hereby corrected as shown below:

On the title page: Item [56]

Page 2, lines 12-13, "Immunosuppriession" should be --Immunosuppression--.

Page 2, line 22, "activationof" should be --activation of--.

Page 2, line 36, "hepatic" should be --Hepatic--.

Col. 1, line 53, "PICA" should be --PKA--.

Col. 6, line 17, "supra" should be --*supra*--.

Col. 6, line 28, "PICA" should be --PKA--.

Col. 6, line 55, "supra" should be --*supra*--.

Col. 7, line 4, "fried" should be --filled--.

Col. 8, line 4, "AKAP79" should be --AKAP 79--.

Col. 8, line 55, "mining" should be --turning--.

UNITED STATES PATENT AND TRADEMARK OFFICE
CERTIFICATE OF CORRECTION

PATENT NO. : 5,629,163

DATED : May 13, 1997

INVENTOR(S) : SCOTT, et al.

It is certified that error appears in the above-identified patent and that said Letters Patent is hereby corrected as shown below:

Col. 8, line 66, "Pepstalin" should be --Pepstatin--.

Col. 8, line 67, "ID" should be --II--.

Col. 10, line 47, "an" should be --art--.

Signed and Sealed this

Ninth Day of December, 1997

BRUCE LEHMAN

Attest:

*Attesting Officer*　　　*Commissioner of Patents and Trademarks*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Arg Arg Lys Arg Ser Gln Ser Ser Lys Glu Glu Lys Pro
 1               5                   10
```

(2) INFORMATION FOR SEQ ID NO:2:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Arg Arg Lys Arg Ser Gln Ser Ser Lys Glu Glu Lys Pro Leu Gln
 1               5                   10                  15
```

(2) INFORMATION FOR SEQ ID NO:3:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Arg Arg Lys Arg Ser Gln Ser Ser Lys Glu Glu Lys Pro Phe Lys
 1               5                   10                  15
```

(2) INFORMATION FOR SEQ ID NO:4:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Asp Leu Ile Glu Glu Ala Ala Val Ser Arg Ile Val Asp Ala Val Ile
 1               5                   10                  15

Glu Glu Val Lys Ala Ala Gly Ala
                20
```

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Gly Arg Arg Asn Ala Ile His Asp Ile
 1               5
```

(2) INFORMATION FOR SEQ ID NO:6:

(i) SEQUENCE CHARACTERISTICS:
        (A) LENGTH: 2257 base pairs
        (B) TYPE: nucleic acid
        (C) STRANDEDNESS: single
        (D) TOPOLOGY: linear (ii) MOLECULE TYPE: cDNA ( i x ) FEATURE:
    ( A ) NAME/KEY: CDS
    ( B ) LOCATION: 1..1461

( x i ) SEQUENCE DESCRIPTION: SEQ ID NO:6:

| | | | | | | | | | | | | | | | | |
|---|---|---|---|---|---|---|---|---|---|---|---|---|---|---|---|---|
| CCG | CCC | CCG | CCC | CCG | CCC | CCA | CCG | CCC | CCT | CTC | GGG | GCC | GAC | CGC | GTC | 48 |
| Pro 1 | Pro | Pro | Pro | Pro 5 | Pro | Pro | Pro | Pro | Pro 10 | Leu | Gly | Ala | Asp | Arg 15 | Val | |
| GTC | AAA | GCT | GTT | CCT | TTT | CCC | CCA | ACT | CAT | CGG | CTG | ACA | TCT | GAA | GAA | 96 |
| Val | Lys | Ala | Val 20 | Pro | Phe | Pro | Pro | Thr | His 25 | Arg | Leu | Thr | Ser | Glu 30 | Glu | |
| GTG | TTT | GAT | ATG | GAT | GGG | ATA | CCC | AGG | GTT | GAT | GTT | CTG | AAG | AAC | CAC | 144 |
| Val | Phe | Asp 35 | Met | Asp | Gly | Ile | Pro 40 | Arg | Val | Asp | Val | Leu 45 | Lys | Asn | His | |
| TTG | GTA | AAA | GAA | GGG | CGG | GTG | GAT | GAA | GAA | ATT | GCA | CTA | AGA | ATT | ATC | 192 |
| Leu | Val 50 | Lys | Glu | Gly | Arg 55 | Val | Asp | Glu | Glu | Ile 60 | Ala | Leu | Arg | Ile | Ile | |
| AAT | GAG | GGT | GCT | GCC | ATA | CTT | CGG | CGG | GAG | AAA | ACC | ATG | ATA | GAA | GTA | 240 |
| Asn 65 | Glu | Gly | Ala | Ala | Ile 70 | Leu | Arg | Arg | Glu | Lys 75 | Thr | Met | Ile | Glu | Val 80 | |
| GAA | GCT | CCA | ATT | ACA | GTG | TGT | GGT | GAC | ATC | CAT | GGC | CAA | TTT | TTT | GAT | 288 |
| Glu | Ala | Pro | Ile | Thr 85 | Val | Cys | Gly | Asp | Ile 90 | His | Gly | Gln | Phe | Phe 95 | Asp | |
| CTG | ATG | AAA | CTT | TTT | GAA | GTA | GGA | GGA | TCA | CCT | GCT | AAT | ACA | CGA | TAC | 336 |
| Leu | Met | Lys | Leu 100 | Phe | Glu | Val | Gly | Gly 105 | Ser | Pro | Ala | Asn | Thr 110 | Arg | Tyr | |
| CTT | TTT | CTT | GGT | GAT | TAT | GTG | GAC | AGA | GGT | TAT | TTT | AGT | ATA | GAG | TGT | 384 |
| Leu | Phe | Leu 115 | Gly | Asp | Tyr | Val | Asp 120 | Arg | Gly | Tyr | Phe | Ser 125 | Ile | Glu | Cys | |
| GTC | TTA | TAT | TTA | TGG | GTC | TTG | AAG | ATT | CTA | TAC | CCA | AGC | ACA | TTA | TTC | 432 |
| Val | Leu 130 | Tyr | Leu | Trp | Val | Leu 135 | Lys | Ile | Leu | Tyr | Pro 140 | Ser | Thr | Leu | Phe | |
| CTT | CTG | AGA | GGC | AAC | CAT | GAA | TGC | AGA | CAC | CTT | ACT | GAA | TAT | TTT | ACC | 480 |
| Leu | Leu | Arg 145 | Gly | Asn | His | Glu 150 | Cys | Arg | His | Leu | Thr 155 | Glu | Tyr | Phe | Thr 160 | |
| TTT | AAG | CAG | GAA | TGT | AAA | ATT | AAA | TAT | TCA | GAA | AGA | GTC | TAT | GAA | GCT | 528 |
| Phe | Lys | Gln | Glu | Cys 165 | Lys | Ile | Lys | Tyr | Ser 170 | Glu | Arg | Val | Tyr | Glu 175 | Ala | |
| TGT | ATG | GAG | GCT | TTT | GAC | AGC | TTG | CCC | CTT | GCT | GCA | CTT | CTA | AAC | CAA | 576 |
| Cys | Met | Glu | Ala 180 | Phe | Asp | Ser | Leu | Pro 185 | Leu | Ala | Ala | Leu | Leu 190 | Asn | Gln | |
| CAA | TTT | CTT | TGT | GTT | CAT | GGT | GGA | CTT | TCA | CCA | GAA | ATA | CAC | ACA | CTG | 624 |
| Gln | Phe | Leu 195 | Cys | Val | His | Gly | Gly 200 | Leu | Ser | Pro | Glu | Ile 205 | His | Thr | Leu | |
| GAT | GAT | ATT | AGG | AGA | TTA | GAT | AGA | TTT | AAA | GAG | CCA | CCT | GCA | TTT | GGA | 672 |
| Asp | Asp | Ile | Arg 210 | Arg | Leu | Asp | Arg | Phe 215 | Lys | Glu | Pro | Pro | Ala 220 | Phe | Gly | |
| CCA | ATG | TGT | GAC | TTG | CTA | TGG | TCT | GAT | CCT | TCT | GAA | GAC | TTT | GGA | AAT | 720 |
| Pro 225 | Met | Cys | Asp | Leu | Leu 230 | Trp | Ser | Asp | Pro | Ser 235 | Glu | Asp | Phe | Gly | Asn 240 | |
| GAA | AAA | TCA | CAA | GAA | CAT | TTT | AGT | CAT | AAT | ACA | GTT | CGA | GGA | TGT | TCT | 768 |
| Glu | Lys | Ser | Gln | Glu 245 | His | Phe | Ser | His | Asn 250 | Thr | Val | Arg | Gly | Cys 255 | Ser | |
| TAT | TTT | TAT | AAC | TAT | CCA | GCA | GTG | TGT | GAA | TTT | TTG | CAA | AAC | AAT | AAT | 816 |
| Tyr | Phe | Tyr | Asn 260 | Tyr | Pro | Ala | Val | Cys 265 | Glu | Phe | Leu | Gln | Asn 270 | Asn | Asn | |
| TTG | TTA | TCG | ATT | ATT | AGA | GCT | CAT | GAA | GCT | CAA | GAT | GCA | GGC | TAT | AGA | 864 |
| Leu | Leu | Ser 275 | Ile | Ile | Arg | Ala | His 280 | Glu | Ala | Gln | Asp | Ala 285 | Gly | Tyr | Arg | |
| ATG | TAC | AGA | AAA | AGT | CAA | ACT | ACA | GGG | TTT | CCT | TCA | TTA | ATA | ACA | ATT | 912 |

|     |     |     |     |     |     |     |     |     |     |     |     |     |     |     |       |
|-----|-----|-----|-----|-----|-----|-----|-----|-----|-----|-----|-----|-----|-----|-----|-------|
| Met | Tyr | Arg | Lys | Ser | Gln | Thr | Thr | Gly | Phe | Pro | Ser | Leu | Ile | Thr | Ile   |
|     | 290 |     |     |     | 295 |     |     |     |     | 300 |     |     |     |     |       |
| TTT | TCG | GCA | CCT | AAT | TAC | TTA | GAT | GTC | TAC | AAT | AAT | AAA | GCT | GCT | GTA   | 960 |
| Phe | Ser | Ala | Pro | Asn | Tyr | Leu | Asp | Val | Tyr | Asn | Asn | Lys | Ala | Ala | Val   |
| 305 |     |     |     |     | 310 |     |     |     |     | 315 |     |     |     |     | 320   |
| CTA | AAG | TAT | GAA | AAT | AAT | GTG | ATG | AAC | ATT | CGA | CAG | TTT | AAT | TGC | TCT   | 1008 |
| Leu | Lys | Tyr | Glu | Asn | Asn | Val | Met | Asn | Ile | Arg | Gln | Phe | Asn | Cys | Ser   |
|     |     |     |     | 325 |     |     |     |     | 330 |     |     |     |     | 335 |       |
| CCA | CAT | CCT | TAT | TGG | TTG | CCC | AAT | TTT | ATG | GAT | GTC | TTT | ACA | TGG | TCC   | 1056 |
| Pro | His | Pro | Tyr | Trp | Leu | Pro | Asn | Phe | Met | Asp | Val | Phe | Thr | Trp | Ser   |
|     |     |     | 340 |     |     |     |     | 345 |     |     |     |     | 350 |     |       |
| TTA | CCA | TTT | GTT | GGA | GAA | AAA | GTG | ACA | GAA | ATG | TTG | GTA | AAT | GTT | CTG   | 1104 |
| Leu | Pro | Phe | Val | Gly | Glu | Lys | Val | Thr | Glu | Met | Leu | Val | Asn | Val | Leu   |
|     |     | 355 |     |     |     |     | 360 |     |     |     |     | 365 |     |     |       |
| AGT | ATT | TGT | TCT | GAT | GAT | GAA | CTA | ATG | ACA | GAA | GGT | GAA | GAC | CAG | TTT   | 1152 |
| Ser | Ile | Cys | Ser | Asp | Asp | Glu | Leu | Met | Thr | Glu | Gly | Glu | Asp | Gln | Phe   |
|     | 370 |     |     |     |     | 375 |     |     |     |     | 380 |     |     |     |       |
| GAT | GTA | GGT | TCA | GCT | GCA | GCC | CGG | AAA | GAA | ATA | ATA | AGA | AAC | AAG | ATC   | 1200 |
| Asp | Val | Gly | Ser | Ala | Ala | Ala | Arg | Lys | Glu | Ile | Ile | Arg | Asn | Lys | Ile   |
| 385 |     |     |     |     | 390 |     |     |     |     | 395 |     |     |     |     | 400   |
| CGA | GCA | ATT | GGC | AAG | ATG | GCA | AGA | GTC | TTC | TCT | GTT | CTC | AGG | GAG | GAG   | 1248 |
| Arg | Ala | Ile | Gly | Lys | Met | Ala | Arg | Val | Phe | Ser | Val | Leu | Arg | Glu | Glu   |
|     |     |     |     | 405 |     |     |     |     | 410 |     |     |     |     | 415 |       |
| AGT | GAA | AGC | GTG | CTG | ACA | CTC | AAG | GGC | CTG | ACT | CCC | ACA | GGG | ATG | TTG   | 1296 |
| Ser | Glu | Ser | Val | Leu | Thr | Leu | Lys | Gly | Leu | Thr | Pro | Thr | Gly | Met | Leu   |
|     |     |     | 420 |     |     |     |     | 425 |     |     |     |     | 430 |     |       |
| CCT | AGT | GGA | GTG | TTG | GCT | GGA | GGA | CGG | CAG | ACC | TTG | CAA | AGT | GGT | AAT   | 1344 |
| Pro | Ser | Gly | Val | Leu | Ala | Gly | Gly | Arg | Gln | Thr | Leu | Gln | Ser | Gly | Asn   |
|     |     | 435 |     |     |     |     | 440 |     |     |     |     | 445 |     |     |       |
| GAT | GTT | ATG | CAA | CTT | GCT | GTG | CCT | CAG | ATG | GAC | TGG | GGC | ACA | ACT | CAC   | 1392 |
| Asp | Val | Met | Gln | Leu | Ala | Val | Pro | Gln | Met | Asp | Trp | Gly | Thr | Thr | His   |
|     | 450 |     |     |     |     | 455 |     |     |     |     | 460 |     |     |     |       |
| TCT | TTT | GCT | AAC | AAT | ACA | CAT | AAT | GCA | TGC | AGG | GAA | CTC | CTT | CTG | CTT   | 1440 |
| Ser | Phe | Ala | Asn | Asn | Thr | His | Asn | Ala | Cys | Arg | Glu | Leu | Leu | Leu | Leu   |
| 465 |     |     |     |     | 470 |     |     |     |     | 475 |     |     |     |     | 480   |
| TTT | AGT | TCC | TGT | CTT | AGC | AGC | TGACATATGC AGGGTATTAT GTGATAGGCA              | 1491 |
| Phe | Ser | Ser | Cys | Leu | Ser | Ser |                                               |      |
|     |     |     |     | 485 |     |     |                                               |      |

```
TCTGATTAGT ACCTGGCCAG GGCATAATAT TGATAGAACA AGTTGTCTTT TAACTGAAAA     1551
TAACAATCAG TTTCCCAGAT TTTCATAAGG TGATATGGGG AGCAGCTCAT GTCATAATTC     1611
CGAAATATTT ATTCATTTGT TTAATGCACC CCTTTCTTTC AAAAGCCTCA GTCAAGAATG     1671
TGAATCAGGG ATATATCTAT ATATCTATTT ACACACATAC ATAAATATAT ATAACTAAAA     1731
TGGAAATGTA ATTCCGAGTT TCTTACTTTT AAAATTTACG TAATTGTATT AGATTTTGCT     1791
TATGTTTTCA AGTATTTATT TTTTGAGTTA AAATTCTGCT TAGGCCCCAA AACTTCCTTT     1851
ATGCACTCAT TTGCCAAAAG ATTTATGCTA AATTTTGTAC CCTGGTAAAT GATTAGAGTT     1911
TGTTTCTGT  GGTGTTTGTC AAACGTTCTA TGTATAATTG ACTGTCTGTA ACATGCTGTT     1971
TCCTTCCTCT GCAGATATAG CTGCTTTCCT AAATCTGTCT GTCTTTCTTT AGGATAGCTG     2031
TATGTCTGTA AATATATGTT CAATTAAATT ACTCTATCAG ACGCTTGTCT GTCTTTTGAT     2091
GTAGAAGCAA CTTTGTAGCA CCTTGATTTT AGGTTTGCTG CATTTGTTGC TGCACTTGGT     2151
TCAGTCTGAA TATGAATGTA ACATTAGATA TTGAGCTATT GTTATAAAGG GTTGAATTTA     2211
AATCATGTAA GTCAAAATTG AAAGGGTGTT ATAAAGTGTG CCTTTA                   2257
```

( 2 ) INFORMATION FOR SEQ ID NO:7:

(i) SEQUENCE CHARACTERISTICS:
(A) LENGTH: 487 amino acids
(B) TYPE: amino acid
(D) TOPOLOGY: linear (ii) MOLECULE TYPE: protein (xi) SEQUENCE DESCRIPTION: SEQ ID NO:7:

| Pro | Pro | Pro | Pro | Pro | Pro | Pro | Pro | Pro | Pro | Leu | Gly | Ala | Asp | Arg | Val |
|---|---|---|---|---|---|---|---|---|---|---|---|---|---|---|---|
| 1 | | | | 5 | | | | | 10 | | | | | 15 | |

| Val | Lys | Ala | Val | Pro | Phe | Pro | Pro | Thr | His | Arg | Leu | Thr | Ser | Glu | Glu |
|---|---|---|---|---|---|---|---|---|---|---|---|---|---|---|---|
| | | | 20 | | | | 25 | | | | | 30 | | | |

| Val | Phe | Asp | Met | Asp | Gly | Ile | Pro | Arg | Val | Asp | Val | Leu | Lys | Asn | His |
| | | 35 | | | | | 40 | | | | | 45 | | | |

| Leu | Val | Lys | Glu | Gly | Arg | Val | Asp | Glu | Glu | Ile | Ala | Leu | Arg | Ile | Ile |
| | 50 | | | | | 55 | | | | | 60 | | | | |

| Asn | Glu | Gly | Ala | Ala | Ile | Leu | Arg | Arg | Glu | Lys | Thr | Met | Ile | Glu | Val |
| 65 | | | | | 70 | | | | 75 | | | | | | 80 |

| Glu | Ala | Pro | Ile | Thr | Val | Cys | Gly | Asp | Ile | His | Gly | Gln | Phe | Phe | Asp |
| | | | | 85 | | | | | 90 | | | | | 95 | |

| Leu | Met | Lys | Leu | Phe | Glu | Val | Gly | Gly | Ser | Pro | Ala | Asn | Thr | Arg | Tyr |
| | | | 100 | | | | | 105 | | | | | 110 | | |

| Leu | Phe | Leu | Gly | Asp | Tyr | Val | Asp | Arg | Gly | Tyr | Phe | Ser | Ile | Glu | Cys |
| | | | 115 | | | | | 120 | | | | | 125 | | |

| Val | Leu | Tyr | Leu | Trp | Val | Leu | Lys | Ile | Leu | Tyr | Pro | Ser | Thr | Leu | Phe |
| | 130 | | | | | 135 | | | | | 140 | | | | |

| Leu | Leu | Arg | Gly | Asn | His | Glu | Cys | Arg | His | Leu | Thr | Glu | Tyr | Phe | Thr |
| 145 | | | | | 150 | | | | | 155 | | | | | 160 |

| Phe | Lys | Gln | Glu | Cys | Lys | Ile | Lys | Tyr | Ser | Glu | Arg | Val | Tyr | Glu | Ala |
| | | | | 165 | | | | | 170 | | | | | 175 | |

| Cys | Met | Glu | Ala | Phe | Asp | Ser | Leu | Pro | Leu | Ala | Ala | Leu | Leu | Asn | Gln |
| | | | 180 | | | | | 185 | | | | | 190 | | |

| Gln | Phe | Leu | Cys | Val | His | Gly | Gly | Leu | Ser | Pro | Glu | Ile | His | Thr | Leu |
| | | | 195 | | | | | 200 | | | | | 205 | | |

| Asp | Asp | Ile | Arg | Arg | Leu | Asp | Arg | Phe | Lys | Glu | Pro | Pro | Ala | Phe | Gly |
| | 210 | | | | | 215 | | | | | 220 | | | | |

| Pro | Met | Cys | Asp | Leu | Leu | Trp | Ser | Asp | Pro | Ser | Glu | Asp | Phe | Gly | Asn |
| 225 | | | | | 230 | | | | | 235 | | | | | 240 |

| Glu | Lys | Ser | Gln | Glu | His | Phe | Ser | His | Asn | Thr | Val | Arg | Gly | Cys | Ser |
| | | | | 245 | | | | | 250 | | | | | 255 | |

| Tyr | Phe | Tyr | Asn | Tyr | Pro | Ala | Val | Cys | Glu | Phe | Leu | Gln | Asn | Asn | Asn |
| | | | 260 | | | | | 265 | | | | | 270 | | |

| Leu | Leu | Ser | Ile | Ile | Arg | Ala | His | Glu | Ala | Gln | Asp | Ala | Gly | Tyr | Arg |
| | | 275 | | | | | 280 | | | | | 285 | | | |

| Met | Tyr | Arg | Lys | Ser | Gln | Thr | Thr | Gly | Phe | Pro | Ser | Leu | Ile | Thr | Ile |
| | 290 | | | | | 295 | | | | | 300 | | | | |

| Phe | Ser | Ala | Pro | Asn | Tyr | Leu | Asp | Val | Tyr | Asn | Asn | Lys | Ala | Ala | Val |
| 305 | | | | | 310 | | | | | 315 | | | | | 320 |

| Leu | Lys | Tyr | Glu | Asn | Asn | Val | Met | Asn | Ile | Arg | Gln | Phe | Asn | Cys | Ser |
| | | | | 325 | | | | | 330 | | | | | 335 | |

| Pro | His | Pro | Tyr | Trp | Leu | Pro | Asn | Phe | Met | Asp | Val | Phe | Thr | Trp | Ser |
| | | | 340 | | | | | 345 | | | | | 350 | | |

| Leu | Pro | Phe | Val | Gly | Glu | Lys | Val | Thr | Glu | Met | Leu | Val | Asn | Val | Leu |
| | | 355 | | | | | 360 | | | | | 365 | | | |

| Ser | Ile | Cys | Ser | Asp | Asp | Glu | Leu | Met | Thr | Glu | Gly | Glu | Asp | Gln | Phe |
| | 370 | | | | | 375 | | | | | 380 | | | | |

```
Asp Val Gly Ser Ala Ala Ala Arg Lys Glu Ile Ile Arg Asn Lys Ile
385             390             395                         400

Arg Ala Ile Gly Lys Met Ala Arg Val Phe Ser Val Leu Arg Glu Glu
            405             410                         415

Ser Glu Ser Val Leu Thr Leu Lys Gly Leu Thr Pro Thr Gly Met Leu
            420             425                     430

Pro Ser Gly Val Leu Ala Gly Gly Arg Gln Thr Leu Gln Ser Gly Asn
        435             440                     445

Asp Val Met Gln Leu Ala Val Pro Gln Met Asp Trp Gly Thr Thr His
    450             455                 460

Ser Phe Ala Asn Asn Thr His Asn Ala Cys Arg Glu Leu Leu Leu Leu
465             470                 475                     480

Phe Ser Ser Cys Leu Ser Ser
            485
```